United States Patent [19]
Ohmae et al.

[11] Patent Number: 5,959,155
[45] Date of Patent: Sep. 28, 1999

[54] PROCESS FOR THE EXTRACTION OF HYDROPEROXIDES

[75] Inventors: Toshikazu Ohmae; Shigefumi Tokumasu; Hideo Ohki, all of Chiba, Japan

[73] Assignee: Sumitomo Chemical Company, Limited, Osaka, Japan

[21] Appl. No.: 08/988,182

[22] Filed: Dec. 10, 1997

[30] Foreign Application Priority Data

Dec. 19, 1996 [JP] Japan ..................... 8-340188

[51] Int. Cl.$^6$ .................................. C07C 409/00
[52] U.S. Cl. ............................. 568/576; 568/568
[58] Field of Search ..................... 568/568, 576

[56] References Cited

U.S. PATENT DOCUMENTS 4,059,637  11/1977  Hosaka .

FOREIGN PATENT DOCUMENTS 49-20135  2/1974  Japan .
57-38579  8/1982  Japan .

OTHER PUBLICATIONS

Aldrich chem handbook, p. 1015, 1996.
CA:81:145429 ab of "Determination of the composition of a reaction mixture after the acod decomposition of cumene hydroperoxide", by Pankova, Khim Ind (Sofia) 46(5) pp. 219–220, 1974.
CA:102:220556 abs of JP59212440, 1984.

*Primary Examiner*—Gary Geist
*Assistant Examiner*—Jean F Vollano
*Attorney, Agent, or Firm*—Sughrue, Mion, Zinn, Macpeak & Seas, PLLC

[57] ABSTRACT

A process for extraction of hydroperoxides wherein 1,3-di-(2-hydroperoxy-2-propyl)benzene and 3-(2-hydroxy-2-propyl)-1-(2-hydroperoxy-2-propyl)benzene are extracted from a raw solution comprising 1,3-di-(2-hydroperoxy-2-propyl)benzene, 3-(2-hydroxy-2-propyl)-1-(2-hydroperoxy-2-propyl)benzene and an aqueous sodium hydroxide solution, said process using methyl isobutyl ketone containing not more than 10 ppm by weight of a phenol or phenols as a solvent for extraction.

8 Claims, No Drawings

PROCESS FOR THE EXTRACTION OF HYDROPEROXIDES

The present invention relates to a process for extraction of hydroperoxides. More precisely, the present invention relates to a process for extraction of hydroperoxides wherein 1,3-di-(2-hydroperoxy-2-propyl)benzene (hereinafter referred to as DHPO) and 3-(2-hydroxy-2-propyl)-1-(2-hydroperoxy-2-propyl)benzene (hereinafter referred to as CHPO) are extracted and separated from a raw solution containing DHPO, CHPO and an aqueous sodium hydroxide solution using methyl isobutyl ketone (hereinafter referred to as MIBK) as a solvent for extraction, said process being excellent in phase-separating efficiency and thus holding a dominant position from viewpoints of efficiency and economy in the industrial practice.

The known process for producing resorcinol (hereinafter referred to as RES) involves oxidation of 1,3-diisopropylbenzene (hereinafter, referred to as MDC) to give an oxidation solution containing DHPO and CHPO, and acid cleavage of DHPO in said oxidation solution to convert it into RES. Usually, the oxidation solution is extracted with an aqueous sodium hydroxide solution to give an aqueous sodium hydroxide solution containing DHPO and CHPO. For the extraction of DHPO and CHPO from the aqueous solution, an extracting procedure using a solvent for extraction such as MIBK or the like can be applied. The conventional process had, however, a problem that the phase-separating efficiency during the extraction is inferior so that the phases become difficult to be separated.

Under these circumstances, the present inventors studied to improve the process for extraction of DHPO and CHPO from a solution as a raw material containing DHPO, CHPO and aqueous sodium hydroxide using MIBK as a solvent for extraction, and found the fact that the phase-separating efficiency becomes inferior when a phenol or phenols is or are present even if in a small quantity. Based on such finding, they have succeeded in providing a process for extraction in which phase-separating efficiency during extraction is excellent.

That is, the present invention relates to a process for extraction of hydroperoxides wherein DHPO and CHPO are extracted from a raw solution containing DHPO, CHPO and an aqueous sodium hydroxide solution, said process using MIBK containing not more than 10 ppm by weight of a phenol or phenols as a solvent for extraction.

The raw solution used in the present invention is a solution containing DHPO, CHPO and an aqueous sodium hydroxide solution. Such solution includes an aqueous solution obtained by extracting an oxidation solution, formed by oxidizing MDC in the course of producing RES as described above, with an aqueous sodium hydroxide solution, but is not limited thereof.

It is preferred that the total content of DHPO and CHPO in the raw solution is 1 to 20% by weight.

The present invention is directed to a process for extracting DHPO and CHPO from the raw solution. DHPO and CHPO are separated and recovered individually in some case or separated and recovered in combination thereof. The present invention encompasses the both cases.

As the solvent for extraction, MIBK containing not more than 10 ppm by weight, preferably not more than 1 ppm, of a phenol or phenols is used. The fact that the content of a phenol or phenols in the solvent limited within the specified range is the most important feature of the present invention. If the content of a phenol or phenols is greater than that range, the phase-separating efficiency during the extraction becomes inferior. The phenol or phenols include(s) 3-(2-propenyl)phenol (hereinafter, referred to as OST) and/or RES and the like. Said content of the phenol or phenols is based on the total amount of all the phenols contained therein.

It is preferred that the weight of MIBK used in the extraction is 4 to 20 times as much as the total weight of DHPO and CHPO in the raw solution to be subjected to the extraction. If the weight is smaller than the above range, the extraction is not sufficiently effected in some cases. To the contrary, if the weight is greater than that range, the working may become uneconomical.

It is also preferred that the temperature of the solution under extraction is 20 to 80° C. If the temperature of the solution is lower than the above range, the extraction is not sufficiently effected or the phase-separating efficiency during the extraction becomes inferior in some cases. To the contrary, if the temperature of the solution is higher than the above range, the rate of decomposition of DHPO and/or CHPO may become fast.

The extraction may be carried out in an apparatus such as an extraction tower, a mixer-settler or the like.

It is preferred that MIBK used in the extraction is recovered after purification and recycled for use in the next extraction.

Preferred process for purification and recovery includes a process comprising the following cleavage step and purification step:

cleavage step: a step wherein a MIBK solution containing DHPO and/or CHPO used in the extraction is reacted with an acid to convert DHPO and/or CHPO into RES and/or OST, respectively, thereby giving a MIBK solution containing RES and/or OST; and purification step: a step wherein the MIBK solution obtained in the cleavage step is neutralized and the neutralized MIBK solution is subjected to distillation or to distillation plus wash with an aqueous alkali to give the purified, recovered MIBK.

Specific embodiments of the present invention include, for example, a process wherein a raw solution containing DHPO, CHPO and an aqueous sodium hydroxide solution and MIBK are supplied to an extracting region, and a MIBK solution containing DHPO, a MIBK solution containing CHPO and an aqueous sodium hydroxide are obtained. DHPO and CHPO may either be recovered independently as described above or recovered in a solution in MIBK containing both of DHPO and CHPO. Further, the extracting region may either be present in a single apparatus or in two or more separate apparatuses.

EXAMPLES

The present invention will now be described by means of Examples. It is needless to say that these Examples should not be construed as a limitation upon the scope of the present invention.

Example 1 and Comparative Example 1

The raw solution was an aqueous solution containing 12% by weight of DHPO, 3% by weight of CHPO and 6% by weight of sodium hydroxide obtained by extracting an oxidation solution, formed by oxidizing MDC, with an aqueous sodium hydroxide. An extraction tower was used as the apparatus for extraction. The temperature during extraction was 30–60° C. The amount of the raw solution supplied was 100 parts by weight and the rate of supplying MIBK as the extraction solvent was 70 parts by weight. After extraction, a MIBK solution containing DHPO, a MIBK solution containing CHPO and an aqueous sodium hydroxide solution were obtained separately. The content of phenols in MIBK as the extraction solvent was varied and phase-separating efficiency upon extraction was examined in respective cases. The judgement of the phase-separating efficiency was evaluated by placing the solution after extraction in a transparent container and visually observing. The score and criteria for evaluation were as follows: o, good; X, bad. Conditions and results are shown in Table 1.

Example 2

The procedure in Example 1 was substantially repeated except that the raw solution was an aqueous solution containing 13% by weight of DHPO, 0.4% by weight of CHPO and 6% by weight of sodium hydroxide, the liquid temperature was 60° C., and a MIBK solution containing DHPO and CHPO, and an aqueous sodium hydroxide solution were obtained separately after extraction. The results are shown in Table 1.

TABLE 1

|  | Example | | Comparative example |
|---|---|---|---|
|  | 1 | 2 | 1 |
| Concentration of Phenols*1 | | | |
| OST wt ppm | ≦0.1 | ≦0.1 | 15 |
| RES wt ppm | ≦0.1 | ≦0.1 | ≦0.1 |
| Total wt ppm | ≦0.1 | ≦0.1 | 15 |
| Phase-separating Efficiency | o | o | X |

*1 Concentration of Phenols: Concentration of the phenols in MIBK used as the solvent for extraction.
"≦0.1" means that the value was not more than 0.1 ppm by weight.

What is claimed is:

1. A process for recovery of hydroperoxides comprising:
   contacting a raw solution comprising 1,3-di-(2-hydroperoxy-2-propyl)benzene, 3-(2-hydroxy-2-propyl)-1-(2-hydroperoxy-2-propyl)benzene and an aqueous sodium hydroxide solution with methyl isobutyl ketone as a solvent for extraction to extract 1,3-di-(2-hydroperoxy-2-propyl)benzene and 3-(2-hydroxy-2-propyl)-1-(2-hydroperoxy-2-propyl)benzene; and
   recovering with purification used methyl isobutyl ketone;
   wherein the methyl isobutyl ketone used for contacting said raw solution contains not more than 10 ppm by weight of a phenol or phenols and at least a part of the methyl isobutyl ketone used for contacting said raw solution is said used methyl isobutyl ketone.

2. A process for recovery according to claim 1, wherein the phenol or phenols is or are 3-(2-propenyl)phenol and/or resorcinol.

3. A process for recovery according to claim 1, wherein the raw solution is an aqueous solution obtained by extracting an oxidation solution, formed by oxidizing 1,3-diisopropylbenzene, with an aqueous sodium hydroxide solution.

4. A process for recovery according to claim 1, wherein the total content of 1,3-di-(2-hydroperoxy-2-propyl)benzene and 3-(2-hydroxy-2-propyl)-1-(2-hydroperoxy-2-propyl)benzene in the raw solution is 1 to 20% by weight.

5. A process for recovery according to claim 1, wherein the weight of methyl isobutyl ketone used in the extraction is 4 to 20 times as much as the total weight of 1,3-di-(2-hydroperoxy-2-propyl)benzene and 3-(2-hydroxy-2-propyl)-1-(2-hydroperoxy-2-propyl)benzene in the raw solution to be subjected to the extraction.

6. A process for recovery according to claim 1, wherein the temperature of the solution under extraction is 20 to 80° C.

7. A process for recovery according to claim 1, wherein said methyl isobutyl ketone obtained by recovering with purification is methyl isobutyl ketone obtained by the following cleavage step and purification step:
   cleavage step: a step wherein a methyl isobutyl ketone solution containing 1,3-di-(2-hydroperoxy-2-propyl)benzene and/or 3-(2-hydroxy-2-propyl)-1-(2-hydroperoxy-2-propyl)benzene used in the extraction is reacted with an acid to give a methyl isobutyl ketone solution containing resorcinol and/or 3-(2-propenyl)phenol; and
   purification step: a step wherein methyl isobutyl ketone is purified and recovered by neutralizing the methyl isobutyl ketone solution obtained in the cleavage step, and then subjecting the product to distillation or to distillation plus wash with an aqueous alkali.

8. The process for recovery according to claim 1, wherein said methyl isobutyl ketone used for contacting said raw solution contains not more than 1 ppm weight of a phenol or phenols.

* * * * *